US007335808B2

(12) United States Patent
Koper et al.

(10) Patent No.: US 7,335,808 B2
(45) Date of Patent: Feb. 26, 2008

(54) METHOD FOR BIOLOGICAL AND CHEMICAL CONTAMINATION

(75) Inventors: Olga Koper, Manhattan, KS (US); Kenneth J. Klabunde, Manhattan, KS (US); Lisa S. Martin, Manhattan, KS (US); Kyle B. Knappenberger, Manhattan, KS (US); Laura L. Hladky, Manhattan, KS (US); Shawn P. Decker, Manhattan, KS (US)

(73) Assignee: NanoScale Corporation, Manhattan, KS (US)

( * ) Notice: Subject to any disclaimer, the term of this patent is extended or adjusted under 35 U.S.C. 154(b) by 694 days.

(21) Appl. No.: 10/658,011

(22) Filed: Sep. 9, 2003

(65) Prior Publication Data

US 2004/0045479 A1    Mar. 11, 2004

Related U.S. Application Data

(63) Continuation of application No. 09/824,947, filed on Apr. 3, 2001, now Pat. No. 6,653,519, which is a continuation-in-part of application No. 09/549,991, filed on Apr. 14, 2000, now Pat. No. 6,417,423, which is a continuation-in-part of application No. 09/153,437, filed on Sep. 15, 1998, now Pat. No. 6,057,488.

(51) Int. Cl.
*A62D 3/00* (2007.01)
(52) U.S. Cl. .................................... 588/401
(58) Field of Classification Search ............... 588/299, 588/401
See application file for complete search history.

(56) References Cited

U.S. PATENT DOCUMENTS

| | | | |
|---|---|---|---|
| 3,915,350 A | 10/1975 | Davies et al. |
| 3,998,363 A | 12/1976 | Beres et al. |
| 4,659,560 A | 4/1987 | Bews et al. |
| 4,770,715 A | 9/1988 | Mandel et al. |
| 5,262,150 A | 11/1993 | Laugier et al. |
| 5,403,587 A | 4/1995 | McCue et al. |
| 5,463,167 A | 10/1995 | Ou |
| 5,499,587 A | 3/1996 | Rodriquez et al. |
| 5,513,584 A | 5/1996 | Rodriguez et al. |
| 5,547,649 A | 8/1996 | Beck et al. |
| 5,648,591 A | 7/1997 | Donecker et al. |
| 5,712,219 A | 1/1998 | Klabunde et al. |
| 5,759,939 A | 6/1998 | Klabunde et al. |
| 5,914,436 A | 6/1999 | Klabunde et al. |
| 5,939,146 A | 8/1999 | Lavernia |
| 5,968,652 A | 10/1999 | Hanggi et al. |
| 5,985,814 A | 11/1999 | Zocchi et al. |
| 5,990,373 A | 11/1999 | Klabunde |
| 6,025,034 A | 2/2000 | Strutt et al. |
| 6,025,402 A | 2/2000 | Farkas |
| 6,045,925 A | 4/2000 | Klabunde et al. |
| 6,057,488 A | 5/2000 | Koper et al. |
| 6,087,294 A | 7/2000 | Klabunde et al. |
| 6,093,236 A | 7/2000 | Klabunde et al. |
| 6,106,854 A | 8/2000 | Belfer et al. |
| 6,183,785 B1 | 2/2001 | Westfall |
| 6,235,351 B1 | 5/2001 | DiMarzio et al. |
| 6,258,417 B1 | 7/2001 | Goswami et al. |
| 6,264,922 B1 | 7/2001 | Wood et al. |
| 6,276,287 B1 | 8/2001 | Imai et al. |
| 6,294,498 B1 | 9/2001 | Darcissac et al. |
| 6,417,423 B1 | 7/2002 | Koper et al. |
| 6,447,577 B1 | 9/2002 | Espin et al. |
| 6,482,357 B1 | 11/2002 | Fox et al. |
| 6,653,519 B2 | 11/2003 | Koper et al. |
| 2002/0028288 A1 | 3/2002 | Rohrbaugh et al. |
| 2002/0035032 A1 | 3/2002 | Koper et al. |
| 2002/0037256 A1 | 3/2002 | Nocerino et al. |
| 2002/0045010 A1 | 4/2002 | Rohrbaugh et al. |
| 2002/0104801 A1 | 8/2002 | Voute et al. |
| 2003/0012686 A1 | 1/2003 | Andersen et al. |
| 2003/0032192 A1 | 2/2003 | Haubold et al. |

FOREIGN PATENT DOCUMENTS

DE        3622242        1/1988

(Continued)

OTHER PUBLICATIONS

Cleveland Clinic Foundation, Dept of Artifical Organs; P. S. Malchesky, W. Varnes, W. Pixtkiowicz, Y. Nose; Membranes Containing Sorbents for Blood Detoxification; vol. XXIII Trans. Am. Soc. Artif. Intern. Organs, 1977; p. 659-665.

(Continued)

*Primary Examiner*—Edward M. Johnson
(74) *Attorney, Agent, or Firm*—Hovey Williams LLP

(57) ABSTRACT

Compositions and methods for destroying biological agents such as toxins and bacteria are provided wherein the substance to be destroyed is contacted with finely divided metal oxide or hydroxide nanocrystals. In various embodiments, the metal oxide or metal hydroxide nanocrystals have reactive atoms stabilized on their surfaces, species adsorbed on their surfaces, or are coated with a second metal oxide. The desired metal oxide or metal hydroxide nanocrystals can be pressed into pellets for use when a powder is not feasible. Preferred metal oxides for the methods include $MgO$, $SrO$, $BaO$, $CaO$, $TiO_2$, $ZrO_2$, $FeO$, $V_2O_3$, $V_2O_5$, $Mn_2O_3$, $Fe_2O_3$, $NiO$, $CuO$, $Al_2O_3$, $SiO_2$, $ZnO$, $Ag_2O$, $[Ce(NO_3)_3$—$Cu(NO_3)_2]TiO_2$, $Mg(OH)_2$, $Ca(OH)_2$, $Al(OH)_3$, $Sr(OH)_2$, $Ba(OH)_2$, $Fe(OH)_3$, $Cu(OH)_3$, $Ni(OH)_2$, $Co(OH)_2$, $Zn(OH)_2$, $AgOH$, and mixtures thereof.

22 Claims, 9 Drawing Sheets

FOREIGN PATENT DOCUMENTS

| JP | 4235121 | 8/1992 |
| --- | --- | --- |
| JP | 08-325467 | 12/1996 |
| JP | 0305230 | 8/1997 |
| JP | 9316435 | 12/1997 |
| JP | 1192478 | 7/1999 |
| JP | 1323195 | 11/1999 |
| JP | 0351940 | 12/2000 |
| JP | 2001574408 | 6/2001 |

OTHER PUBLICATIONS

Elsevier; Catherine Bothe Almquist, Sun-Tak Hwang; The Permeation of Organophosphorus Compounds in Silicone Rubber Membranes; Journal Of Membrane Science; vol. 153, 1999; pp. 57-69.

J. Phys. Chem; George W. Wagner, Olga Koper, Erik Lucas, Shawn Decker, Kenneth J. Klabunde: Reactions of FX, GD and HD With Nanosize CaO: Autocatalytic Dehydrohalogenation of HD; American Chemical Society, vol. 104, 2000; pp. 5118-5123.

Department of Chemistry, Kansas State University; Abbas Khaleel, Pramesh N. Kapoor, Kenneth J. Klabunde; Nanocrystalline Metal Oxides As New Adsorbents for Air Purification; NanoStructured Materials, vol. 11, No. 4, 1999; pp. 459-468.

Department of Chemistry, Kansas State University; E.M. Lucas, K.J. Klabunde; Nanocrystals As Destructive Adsorbants for Mimics of Chemical Warfare Agents; NanoStructured Materials, col. 12, 1999; pp. 179-182.

J. Phys. Chem; George W. Wagner, Phillip W. Bartram, Olga Koper, Kenneth J. Klabunde: Reactions of VX, GD, and HD With Nanosize MgO: American Chemical Society, vol. 103, 1999; pp. 3225-3228.

Department of Chemistry, Kansas State University; Olga B. Koper, Isabelle Lagadic, Alexander Voledin, Kenneth J. Klabunde; Alkaline-Earth Oxide Nanoparticles Obtained by Aerogel Methods, Characterization and Rational for Unexpectedly High Surface Chemical Reactivities; Chemistry of Materials, vol. 9, No. 11, 1997; pp. 2468-2480.

Department of Chemistry, Kansas State University; Kenneth J. Klabunde, Jane Stark, Olga Koper, Cathy Mohs, Dong G. Park, Shawn Decker, Yan Jiang, Isabelle Lagadic, Dajic Zhang; Nanocrystals As Stoichiometric Reagents With Unique Surface Chemistry; J. Phys Chem, vol. 100, 1996; pp. 12142-12153.

Langmuir; P. Somasundaran, E. Fu, Qun Xu; Coadsorption of Anionic and Nonionic Surfactant Mixtures at the Alumina-Water Inferface; Langmuir Center for Colloids and Interfaces, 1992; pp. 1065-1069.

Department of Chemistry, Kansas State University; Yong-Xi Li, Kenneth J. Klabunde; Nanoscale Metal Oxied Particles As Chemical Reagents, Destructive Adsorption of a Chemical Agent Simulant, Dimethyl Methylphosphonate, on Heat-Treated Magnesium Oxide; Langmuir, vol. 7, No. 7, 1991; pp. 1388-1393.

Miami Valley Laboratories; Paul M. Holland; Nonideal mixed Monolayer Model; American Chemical Society, 1986; pp. 102-115.

Applied Surface Science; Zhenghe Xu, Qingxia Liu, J.A. Finch; Silanation and Stability of 3-Aminopropyl Triethoxy Silane on Nanosized Superparamagnetic Particles: I. Direct Silanation; Elsevier Science, col. 120, 1997; pp. 269-278.

American Chemical Society; Chuntao Cao, Alexander Y. Fadeev, Thomas J. McCarthy; Reactions of Organosilanes With Silica Surfaces in Carbon Dioxide; Langmuir, vol. 17, 2001; pp. 757-761.

FIG. 4.

PARTICLE SIZE DISTRIBUTION--BACILLUS GLOBIGII DISSEMINATION
FOLLOWED BY LOW CONCENTRATION POWDER DISPERSION

FIG. 7.

PARTICLE SIZE DISTRIBUTION--BACILLUS GLOBIGII DISSEMINTION FOLLOWED BY HIGH CONCENTRATION POWDER DISPERSION

METHOD FOR BIOLOGICAL AND CHEMICAL CONTAMINATION

RELATED APPLICATION

This is a continuation of application Ser. No. 09/824,947, filed Apr. 3, 2001 now U.S. Pat. No. 6,653,519, which is a continuation-in-part of application Ser. No. 09/549,991, filed Apr. 14, 2000 now U.S. Pat. No. 6,417,423, incorporated by reference herein, which is a continuation-in-part of application Ser. No. 09/153,437, incorporated by reference herein and filed Sep. 15, 1998, now U.S. Pat. No. 6,057,488.

BACKGROUND OF THE INVENTION

1. Field of the Invention

The present invention is broadly concerned with compositions and methods for sorbing and/or destroying dangerous substances such as chemical and biological warfare agents. The methods of the invention are carried out by simply contacting the target substance with particulate metal oxide or metal hydroxide compositions. These compositions can be unmodified, or alternately, can be coated with a second metal oxide or a metal nitrate or mixture of metal nitrates, have reactive atoms or mixtures of reactive atoms stabilized on their surfaces, or have species adsorbed on their surfaces. In another embodiment, the particulate metal oxides or metal hydroxides (unmodified or modified) which can be formed into pellets (e.g., by pressing or other methods such as by using a binder) which possess the same destructive abilities as the metal oxides or metal hydroxide in powder form. Methods in accordance with the invention require the use of minimal liquids, thus resulting in very little effluent. Furthermore, the particulate metal oxide or metal hydroxide compositions utilized in the methods of the invention are not harmful to equipment or to humans and can easily be used directly at the site of contamination.

2. Description of the Prior Art

The threat of biological and chemical warfare has grown considerably in recent times. Numerous countries are capable of developing deadly biological and chemical weapons. Some potent biological agents include the following: bacteria such as *Bacillus anthracis* (anthrax) and *Yersinia pestis* (plague); viruses such as variola virus (small pox) and flaviviruses (hemorrhagic fevers); and toxins such as botulinum toxins and saxitoxin. Some potent chemical agents include: blister or vesicant agents such as mustard agents; nerve agents such as methylphosphonothiolate (VX); lung damaging or choking agents such as phosgene (CG); cyanogen agents such as hydrogen cyanide; incapacitants such as 3-quinuclidinyl benzilate; riot control agents such as CS (malonitrile); smokes such as zinc chloride smokes; and some herbicides such as 2,4-D (2,4-dichlorophenoxy acetic acid).

All of the above agents, as well as numerous other biological and chemical agents, pose a significant risk to private citizens as well as to military personnel. For example, vesicant agents burn and blister the skin or any other part of the body they contact, including eyes, mucus membranes, lungs, and skin. Nerve agents are particularly toxic and are generally colorless, odorless, and readily absorbable through the lungs, eyes, skin, and intestinal track. Even a brief exposure can be fatal and death can occur in as quickly as 1 to 10 minutes. Biological agents such as anthrax are easily disseminated as aerosols and thus have the ability to inflict a large number of casualties over a wide area with minimal logistical requirements. Many biological agents are highly stable and thus can persist for long periods of time in soil or food.

There are currently two general types of decontamination methods for biological agents: chemical disinfection and physical decontamination. Chemical disinfectants, such as hypochlorite solutions, are useful but are corrosive to most metals and fabrics, as well as to human skin. Physical decontamination, on the other hand, usually involves dry heat up to 160° C. for 2 hours, or steam or super-heated steam for about 20 minutes. Sometimes UV light can be used effectively, but it is difficult to develop and standardize for practical use.

These methods have many drawbacks. The use of chemical disinfectants can be harmful to personnel and equipment due to the corrosiveness and toxicity of the disinfectants. Furthermore, chemical disinfectants result in large quantities of effluent which must be disposed of in an environmentally sound manner. Physical decontamination methods are lacking because they require large expenditures of energy. Both chemical and physical methods are difficult to use directly at the contaminated site due to bulky equipment and/or large quantities of liquids which must be transported to the site. Finally, while a particular decontamination or disinfection method may be suitable for biological decontamination, it is generally not effective against chemical agents. There is a need for decontamination compounds which are effective against a wide variety of both chemical and biological agents, have low energy requirements, are easily transportable, do not harm skin or equipment, and employ small amounts of liquids with minimal or no effluent.

SUMMARY OF THE INVENTION

The present invention overcomes these problems and provides compositions and methods for sorbing (e.g., adsorption and chemisorption) and destroying biological and chemical agents. To this end, the invention contemplates the use of finely divided nanoscale metal oxide or metal hydroxide adsorbents. These adsorbents can be used in an unmodified form or can be pelletized, coated with a second metal oxide or a metal nitrate, or have reactive atoms stabilized on their surfaces. These decontamination reactions can be carried out over a wide range of temperatures and can be conducted at the contaminated site. Furthermore, these adsorbents are not harmful to equipment or to humans.

In more detail, the nanoscale adsorbents used in the methods of the invention are formed from metal oxides or metal hydroxides selected from the group consisting of $MgO$, $CeO_2$, $CaO$, $TiO_2$, $ZrO_2$, $FeO$, $V_2O_3$, $V_2O_5$, $Mn_2O_3$, $Fe_2O_3$, $NiO$, $CuO$, $Al_2O_3$, $ZnO$, $SiO_2$, $Ag_2O$, $SrO$, $BaO$, $Mg(OH)_2$, $Ca(OH)_2$, $Al(OH)_3$, $Sr(OH)_2$, $Ba(OH)_2$, $Fe(OH)_3$, $Cu(OH)_3$, $Ni(OH)_2$, $Co(OH)_2$, $Zn(OH)_2$, $AgOH$, and mixtures thereof. While conventionally prepared powders can be used in the methods of the invention, the preferred powders are prepared by aerogel techniques from Utamapanya et al., *Chem. Mater.*, 3:175-181 (1991), incorporated by reference herein.

The adsorbents should have an average crystallite size of up to about 20 nm, preferably from about 3-8 nm, and more preferably 4 nm, and exhibit a Brunauer-Emmett-Teller (BET) multi-point surface area of at least about 70 $m^2/g$, preferably at least about 100 $m^2/g$, more preferably at least about 120 $m^2/g$. In terms of pore radius, the preferred adsorbents should have an average pore radius of at least about 45 Å, more preferably from about 50-100 Å, and most preferably from about 60-75 Å.

These nanoscale adsorbents can be used alone and in their powder form, or they can be modified. For example, the finely divided particles of the metal oxides or metal hydroxides can have at least a portion of their surfaces coated with a quantity of a second metal oxide different than the first metal oxide and selected from oxides of metals selected from the group consisting of Ti, V, Fe, Cu, Ni, Co, Mn, Zn, Al, Ce, Sr, Ba, and mixtures thereof. In preferred forms, the coated metal oxide particles comprise a first metal oxide selected from the group consisting of MgO and CaO, whereas the second metal oxide is preferably ZnO. In another embodiment, the first metal oxides described above are coated with a mixture of metal nitrates such as those selected from the group consisting of $Cu(NO_3)_2$, $Ce(NO_3)_3$, $AgNO_3$, and mixtures thereof. In a preferred embodiment, $TiO_2$ is coated with a mixture of cerium nitrate and copper nitrate to form $[Ce(NO_3)_3—Cu(NO_3)_2]TiO_2$.

For most efficient uses, the particles of the first metal oxide or metal hydroxide should have the average crystallite sizes and multi-point surface areas set forth above. As is conventional in the art, the term "particles" is used herein interchangeably with the term "crystallite." The second metal oxide or metal nitrates should be in the form of an extremely thin layer or coating applied onto the surface of the first metal oxide or metal hydroxide, thus giving an average overall size for the composite of up to about 21 nm, more preferably from about 5-11 nm, and most preferably about 5 nm. Generally, the first metal oxide or metal hydroxide should be present in substantial excess relative to the second metal oxide or metal nitrate. Thus, the first metal oxide or metal hydroxide comprises from about 90-99% by weight of the total composite material, and more preferably from about 95-99% by weight. Correspondingly, the second metal oxide or metal nitrate should comprise from 1-10% by weight of the total composite, and more preferably from about 1-5% by weight. At least 25% of the surface area of the first metal oxide or metal hydroxide particles should be covered with the second oxide or metal nitrate, and more preferably from about 90-100% of this surface area should be covered.

The coated metal oxide or metal hydroxide particles or crystallites of this embodiment are preferably fabricated by first forming the very finely divided first particulate material using known aerogel techniques. Thereafter, the second material is applied onto the surface of the first metal oxide or metal hydroxide as an extremely thin layer, e.g., a monolayer having a thickness on the order of less than 1 nm. For example, nanocrystalline MgO can be prepared and then treated with an iron salt such as iron III (acetylacetonate)$_3$ with the ligands being driven off by heating.

In another embodiment, the methods of the invention utilize particulate metal oxides having reactive atoms (different from those atoms making up the metal oxide) stabilized on the surfaces thereof. In more detail, the metal oxide particulates have oxygen ion moieties on their surfaces with reactive atoms interacted or chemisorbed with those surface oxygen ions. The metal oxide particles are, as with the two previously described embodiments, selected from the group consisting of MgO, $CeO_2$, AgO, SrO, BaO, CaO, $TiO_2$, $ZrO_2$, FeO, $V_2O_3$, $V_2O_5$, $Mn_2O_3$, $Fe_2O_3$, NiO, CuO, $Al_2O_3$, ZnO, $SiO_2$, $Ag_2O$, and mixtures thereof. Furthermore, the particles should have the same average crystallite sizes and surface areas described above. Preferably, the reactive atoms utilized in this embodiment are selected from the group consisting of halogens and Group I metals. When halogens are the reactive atoms being stabilized on the surfaces of the particles, the atoms can be atoms of the same halogen (e.g., only chlorine atoms), or the atoms can be mixtures of atoms of different halogens (e.g., both chlorine and bromine atoms on the metal oxide surfaces).

When stabilizing a Group I metal atom, the atom loading on the metal oxide should be from about 5-40% by weight, preferably from about 10-15% by weight, and more preferably about 12% by weight, based upon the weight of the atom-loaded metal oxide taken as 100%. When stabilizing either a Group I metal atom or a halogen atom, the atom loading on the metal oxide can also be expressed as a concentration of atoms per unit of surface area of the metal oxide i.e., at least about 2 atoms per square nanometer of metal oxide surface area, preferably from about 3-8 atoms per square nanometer of metal oxide surface area, and more preferably from about 4-5 atoms per square nanometer of metal oxide surface area. The preferred Group I metal is potassium, and the preferred halogens are chlorine and bromine.

The surface-stabilized, reactive atom composites are formed by heating a quantity of particulate metal oxide particles to a temperature of at least about 200° C., preferably at least about 300° C., and more preferably to a level of from about 450 to about 500° C. Heating the metal oxide particles to these temperatures removes water from the particles so that the final compositions have a surface hydroxyl concentration of less than about 5 hydroxyl groups per square nanometer of metal oxide surface area, and preferably less than about 4 hydroxyl groups per square nanometer of metal oxide surface area. The particles are preferably allowed to cool to room temperature. The particles are then contacted with a source of reactive atoms, e.g., a compound which dissociates into reactive atoms under the proper reaction conditions. The reactive atoms interact with the metal oxide surface oxygen ions, thus stabilizing the atoms on the oxide surface. As used hereinafter, the terms "stabilized" and "stable" mean that, when the metal oxide-atom adducts are heated to a temperature of about 100° C., less than about 10% of the total weight loss of the adduct is attributable to the reactive atoms desorbing.

In another embodiment, the methods of the invention utilize particulate metal oxides having species different than the metal oxide adsorbed on the surfaces thereof. The metal oxide particles are selected from the group consisting of MgO, $CeO_2$, AgO, SrO, BaO, CaO, $TiO_2$, $ZrO_2$, FeO, $V_2O_3$, $V_2O_5$, $Mn_2O_3$, $Fe_2O_3$, NiO, CuO, $Al_2O_3$, ZnO, $SiO_2$, $Ag_2O$, and mixtures thereof. The particles should have the same average crystallite sizes and surface areas described above. Preferably, the adsorbed species are selected from the group consisting of oxides of Group V elements, oxides of Group VI elements, and ozone. Preferred oxides of Group V and VI elements are $NO_2$ and $SO_2$, respectively.

When adsorbing a species on the metal oxide surfaces, the species loading on the metal oxide should be from about 1-60% by weight, preferably from about 5-40% by weight, and more preferably about 15-25% by weight, based upon the weight of the adsorbed species-metal oxide taken as 100%. The species loading can also be expressed as a concentration of species molecules per unit of surface area of metal oxide. Preferably, there are at least about 2 molecules of the species adsorbed per square nanometer of metal oxide and more preferably at least about 5 molecules. The adsorbed-species, metal oxide composites are formed by contacting a quantity of the desired metal oxide (in an air evacuated flask) with the gaseous species. The sample is allowed to react for about 30 minutes, after which time the excess gaseous species is pumped out.

In yet another embodiment, the methods of the invention contemplate forming the above metal oxide particles and composites including those particles (i.e., unmodified, finely divided metal oxide or metal hydroxide particles, finely divided metal oxide or metal hydroxide particles coated with a second metal oxide, finely divided metal oxide particles having reactive atoms and mixtures of reactive atoms stabilized on the surfaces thereof, and metal oxide particles having species adsorbed on the surfaces thereof) into pellets for use when powdered decontaminants are not feasible. These pellets are formed by pressing a quantity of one of these powdered metal oxide or metal hydroxide composites at a pressure of from about 50-6,000 psi, more preferably from about 500-5000 psi, and most preferably at about 2,000 psi. While pressures are typically applied to the powder by way of an automatic or hydraulic press, one skilled in the art will appreciate that the pellets can be formed by any pressure-applying means or by tumbling, rolling, or other means. Furthermore, a binder or filler can be mixed with the adsorbent powder and the pellets can be formed by pressing the mixture by hand. Agglomerating or agglomerated as used hereinafter includes pressing together of the adsorbent powder as well as pressed-together adsorbent powder. Agglomerating also includes the spraying or pressing of the adsorbent powder (either alone or in a mixture) around a core material other than the adsorbent powder.

In order to effectively carry out the methods of the invention, the pellets should retain at least about 25% of the multi-point surface area/unit mass of the metal hydroxide or metal oxide (whichever was used to form the pellet) particles prior to pressing together thereof. More preferably, the multi-point surface area/unit mass of the pellets will be at least about 50%, and most preferably at least about 90%, of the multi-point surface area/unit mass of the starting metal oxide or metal hydroxide particles prior to pressing. The pellets should retain at least about 25% of the total pore volume of the metal hydroxide or metal oxide particles prior to pressing thereof, more preferably, at least about 50%, and most preferably at least about 90% thereof. In the most preferred forms, the pellets will retain the above percentages of both the multi-point surface area/unit mass and the total pore volume. The pellets normally have a density of from about 0.2 to about 2.0 g/cm$^3$, more preferably from about 0.3 to about 1.0 g/cm$^3$, and most preferably from about 0.4 to about 0.7 g/cm$^3$. The minimum surface-to-surface dimension of the pellets (e.g., diameter in the case of spherical or elongated pellet bodies) is at least about 1 mm, more preferably from about 10-20 mm.

In carrying out the methods of the invention, one or more of the above described metal oxide particle composites are contacted with the target substance to be sorbed, decontaminated or destroyed under conditions for sorbing, decontaminating or destroying at least a portion of the substance. The methods of the invention provide for destructively adsorbing a wide variety of chemical agents, including agents selected from the group consisting of acids, alcohols, compounds having an atom of P, S, N, Se, or Te, hydrocarbon compounds, and toxic metal compounds. The methods of the invention also provide for biocidally adsorbing a wide variety of biological agents including bacteria, fungi, viruses, rickettsiae, chlamydia, and toxins. Utilizing the metal oxide particulate composites in accordance with the methods of the invention is particularly useful for destructively adsorbing biological agents such as bacteria (e.g., gram positive bacteria like *B. subtilis, B. globigii* and *B. cereus* or gram negative bacteria like *E. coli,* and *E. Herbicola*).

The composites are also useful for adsorbing toxins such as Aflatoxins, Botulinum toxins, Clostridium perfringens toxins, Conotoxins, Ricins, Saxitoxins, Shiga toxins, *Staphylococcus aureus* toxins, Tetrodotoxins, Verotoxins, Microcystins (Cyanginosin), Abrins, Cholera toxins, Tetanus toxins, Trichothecene mycotoxins, Modeccins, Volkensins, Viscum Album Lectin 1, *Streptococcal* toxins (e.g., erythrogenic toxin and streptolysins), *Pseudomonas* A toxins, Diphtheria toxins, *Listeria monocytogenes* toxins, *Bacillus anthracis* toxic complexes, *Francisella tularensis* toxins, whooping cough pertussis toxins, *Yersinia pestis* toxic complexes, *Yersinia enterocolytica* enterotoxins, and *Pasteurella* toxins. In another embodiment, the methods of the invention provide for the destructive adsorption of hydrocarbon compounds, both chlorinated and non-chlorinated.

The contacting step can take place over a wide range of temperatures and pressures. For example, the particulate metal oxide or metal hydroxide composites can be taken directly to a contaminated site and contacted with the contaminant and/or contaminated surfaces at ambient temperatures and pressures. Alternately, the contacting step can be carried out at a temperature of from about −40-600° C. If the contacting step is to be carried out under ambient temperatures, preferably the reaction temperature range is from about 10-200° C. If the contacting step is to be carried out under high temperature conditions, then preferably the temperature range for the reaction is from about 350-550° C. If the contacting step is carried out under ambient conditions, the particulate metal oxide or metal hydroxide composites should be allowed to contact the target substance for at least about 0.5 minutes, preferably from about 1-100 minutes, and more preferably from about 1.5-20 minutes. If the contacting step is carried out under high temperatures conditions, then the particulate metal oxide or metal hydroxide composites should be allowed to contact the target substance for at least about 4 seconds, preferably for about 5-20 seconds, and more preferably for about 5-10 seconds.

If the target substance is a biological agent, the contacting step results in at least about a 80% reduction in the viable units of the biological agent, preferably at least about a 90% reduction, and more preferably at least about a 95% reduction. If the target substance is a chemical agent, the contacting step results in at least about 90% reduction in the concentration of the chemical agent, preferably at least about a 95% reduction, and more preferably at least about a 99% reduction.

Those skilled in the art will appreciate the benefits provided by the methods of the invention. In accordance with the invention, military personnel can utilize the particulate metal oxides, metal hydroxides, and composites thereof to neutralize highly toxic substances such as nerve agents and biological agents. These particles and composites can be utilized in their non-toxic ultrafine powder form to decontaminate areas exposed to these agents, or the powders or highly pelletized composites can be utilized in air purification or water filtration devices. Other countermeasure and protective uses for the metal oxide or metal hydroxide particles and composites of the particles include personnel ventilation systems and wide-area surface decontamination. Furthermore, the metal oxide or metal hydroxide composites remain airborne for at least one hour, thus providing effective airborne decontamination of chemical or biological agents. Alternately, the composites can be formulated into a cream or incorporated in or on clothing in order to provide protection to personnel at risk of contacting a dangerous agent.

Unlike currently available decontamination methods, the methods of the invention utilize composites that are non-toxic to humans and non-corrosive to equipment, thus permitting the decontaminated equipment to be put back into use rather than discarded. Furthermore, because the composites are easy to disperse and readily transportable, and because little or no water is required to practice the invention, it is relatively simple to destroy the contaminants at the contaminated site.

BRIEF DESCRIPTION OF THE DRAWINGS

FIG. 4 is a graph illustrating the particle size distribution for the mixture of powder and B. globigii when B. globigii was exposed to a low concentration of Cl/AP-MgO powder;

FIG. 7 is a graph depicting the particle size distribution for a mixture of powder and B. globigii when B. globigii was exposed to a high concentration of Cl/AP-MgO;

DETAILED DESCRIPTION OF THE PREFERRED EMBODIMENTS

Figure 1:
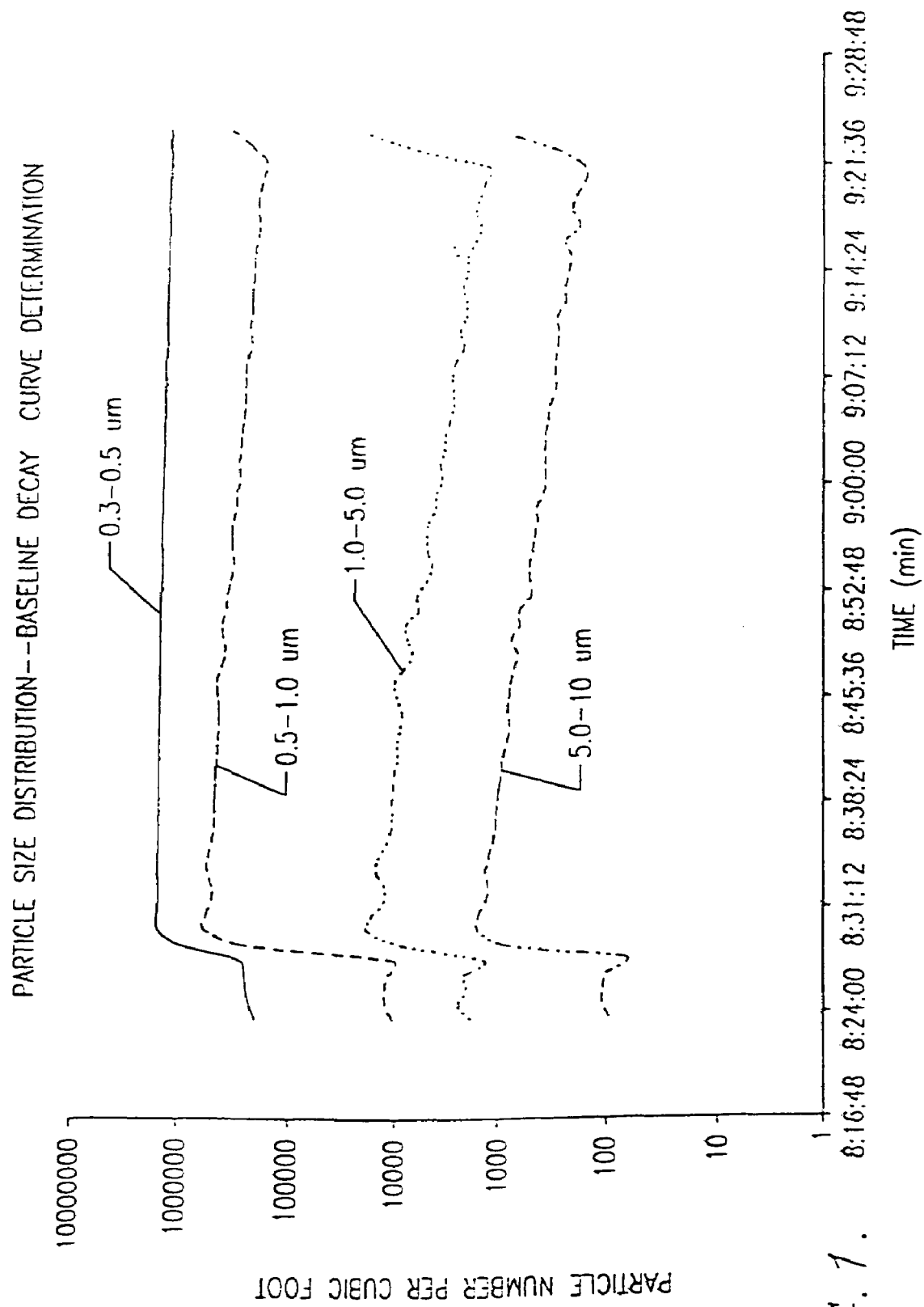
FIG. 1 is a graph illustrating the particle size distribution and particle concentration for B. globigii without the addition of Cl/AP-MgO powder.

The following examples set forth preferred methods in accordance with the invention. It is to be understood, however, that these examples are provided by way of illustration and nothing therein should be taken as a limitation upon the overall scope of the invention. In these examples, "AP-MgO" and "AP-CaO" refer to the respective aerogel (or autoclave) prepared oxides. "CP-MgO" and "CP-CaO" refer to the respective oxides produced by conventional techniques.

EXAMPLE 1

Preparation of MgO Samples

1. AP-MgO

Highly divided nanocrystalline $Mg(OH)_2$ samples were prepared by the autoclave treatment described by Utamapanya et al., Chem. Mater., 3:175-181 (1991), incorporated by reference herein. In this procedure, 10% by weight magnesium methoxide in methanol solution was prepared and 83% by weight toluene solvent was added. The solution was then hydrolyzed by addition of 0.75% by weight water dropwise while the solution was stirred and covered with aluminum foil to avoid evaporation. To ensure completion of the reaction, the mixture was stirred overnight. This produced a gel which was treated in an autoclave using a glass lined 600 ml capacity Parr miniature reactor. The gel solution was placed within the reactor and flushed for 10 minutes with nitrogen gas, whereupon the reactor was closed and pressurized to 100 psi using the nitrogen gas. The reactor was then heated up to 265° C. over a 4 hour period at a heating rate of 1° C./min. The temperature was then allowed to equilibrate at 265° C. for 10 minutes (final reactor pressure was about 800-1000 psi). At this point, the reactor was vented to release the pressure and vent the solvent. Finally, the reactor was flushed with nitrogen gas for 10 minutes. The $Mg(OH)_2$ particles were then thermally converted to MgO. This was accomplished by heating the $Mg(OH)_2$ under dynamic vacuum ($10^{-2}$ Torr) conditions at an ascending temperature rate to a maximum temperature of 500° C. which was held for 6 hours resulting in AP-MgO with a BET surface area of 300-600 $m^2/g$ and an average crystallite size of 4 nm. Further details about the MgO preparation can be found in PCT Publication WO 95/27679, also incorporated by reference herein.

2. CP-MgO

CP-MgO samples were prepared by boiling commercially available MgO (Aldrich Chemical Company) for one hour, followed by microwave drying of the sample. The sample was then dehydrated under vacuum at 500° C. resulting in CP-MgO with a BET surface area of 130-200 $m^2/g$ and an average crystallite size of 8.8 nm.

EXAMPLE 1A

Preparation of AP-CaO and CP-CaO

AP-CaO was prepared in a manner similar to the preparation of AP-MgO as described in Example 1 with the following exceptions: 8 g. of calcium metal and 230 ml of methanol were allowed to react; and 180 ml of toluene and 1.2 ml of distilled water were added to the 20 g of calcium methoxide obtained.

AP-CaO ($N_2$ dehydrated) was prepared in a similar manner with the exception that the sample was dehydrated by heating to a temperature of 500° C. while passing $N_2$ gas over the sample. CP-CaO (vacuum dehydrated) was prepared in the same manner as CP-MgO (described in Example 1, Part 2).

EXAMPLE 1B

Preparation of $Fe_2O_3$/MgO Composites $Mg(OH)_2$ particles were first thermally converted to MgO, followed by deposition of iron oxide to provide the complete composite. The initial thermal conversion of magnesium hydroxide to MgO was carried out by heating the magnesium hydroxide under dynamic vacuum conditions at an ascending temperature rate to a maximum temperature of 500° C., which was held for 6 hours. Most of the dehydration was found to occur at temperatures between 200° C. and 320° C. IR and x-ray diffraction studies confirm virtually complete conversion of the $Mg(OH)_2$ to MgO.

Iron oxide was deposited on the nanoscale MgO particles by carrying out a direct reaction between activated MgO and iron III (acetylacetonate)$_3$, in tetrahydrofuran at room temperature under 1 atmosphere of helium.

In a typical preparation, 0.3 grams of $Mg(OH)_2$ was heated under vacuum ($10^{-3}$ Torr.) at an ascending temperature rate of 1° C./min. to 500° C., which was held for 6 hours to assure complete conversion to MgO, followed by cooling to room temperature.

The evacuated system was then filled with helium at 1 atm. pressure. Two milliliters of 0.25 M iron III (acetylacetonate)$_3$ in tetrahydrofuran (THF) solution (previously prepared under argon by dissolving 4.5 g of iron III (acetylacetonate)$_3$ in 50 ml of THF) was introduced by a syringe. The amount of iron III (acetylacetonate)$_3$ solution used provided the MgO surfaces with 1.4 iron III (acetylacetonate)$_3$ molecules for each surface OH group. The concentration of surface OH groups for the autoclave-prepared MgO was found to be 3.6 OH groups/nm$^2$. The reaction mixture was stirred overnight to allow a complete reaction at room temperature. The reacted Fe$_2$O$_3$/MgO composite was then removed, filtered using regular filter paper, washed with THF to remove any residual iron III (acetylacetonate)$_3$, and dried in air for ten minutes.

IR spectra of the resultant dry product showed bands for the acetylacetonate species, indicating the existence of some acetylacetonate ligands bound to the surfaces of the MgO. This product was heated again under vacuum (10$^{-3}$ Torr.) at 500° C. to remove these ligands.

EXAMPLE 2

Halogenated Metal Oxides

The following procedures were followed to prepare halogenated metal oxides:

1. Chlorinated Metal Oxides

In order to prepare Cl/MgO or Cl/CaO, metal oxide samples (weighing from about 0.30 to about 1.0 g each) were placed in a Schlenk tube (340 ml vacuum tight glass tubes). Each sample tube was evacuated at room temperature and an excess of chlorine gas was allowed to enter the tube at a pressure of about 1 atm of chlorine. The amount of chlorine gas was determined to be an excess amount when the inlet gas remained green. The samples became hot to the touch when the chlorine entered the tubes, indicating that a reaction was taking place. The reaction was complete within one to two minutes, but each sample was allowed to stand for approximately 30 minutes before removal from the tube.

2. Brominated Metal Oxides

Br/MgO and Br/CaO were prepared in a manner similar to that described under Part 1. An excess of bromine gas was allowed to enter a Schlenk tube which contained from 0.30 to 1.0 g of the particular metal oxide sample at the vapor pressure of bromine at room temperature. The amount of bromine gas was determined to be an excess amount when the inlet gas remained dark red. The reaction was complete within several minutes, but each sample was allowed to stand for approximately 30 minutes before removal from the tube.

3. Iodinated Metal Oxides

I/MgO and I/CaO were prepared by placing 1.0 g of the metal oxide in a Schlenk tube along with 1.0 g of iodine. The air was evacuated from the tube, the stopcock was closed, and the mixture was heated to 90-100° C. The iodine vaporized and deposited onto the oxide particles. The sample was allowed to stand for about 30 minutes before removal from the sample tube.

EXAMPLE 3

1. Preparation of *Bacillus globigii* Culture

*B. globigii* was grown for 72 hours at 35° C. on Casitone nutrient agar plates (150 mm, Remel Co., Lenexa, Kans.) containing 0.002% MnCl$_2$ to induce approximately 80% sporulation. For each test, cells were harvested into 25 ml sterile phosphate buffer solution (PBS) and centrifuged at 3000 rpm for 15 minutes. The supernatant was decanted, and the cells were resuspended in 25 ml sterile PBS and vortexed thoroughly. The suspension was diluted to 0.1 O.D.$_{590\ nm}$ (i.e., the suspension was diluted with PBS to 0.1 optical density at the 590 wavenumber) for dissemination using a Bausch and Lomb Spec-20 spectrophotometer.

2. Baseline Decay Characterization for *B. globigii*

A 0.1 O.D.$_{590\ nm}$ suspension of *B. globigii* was disseminated for 30 seconds using a BGI six jet collision nebulizer (CH Technologies, Westwood, N.J.) at 40 psi in a Bioaerosol test chamber. The chamber air was sampled for 60 minutes at a rate of 50 L/min. using two New Brunswick Slit-to-Agar Biological Air Samplers (New Brunswick Scientific Co., Edison, N.J.) with Casitone agar petri plates. The sampling began 1 minute after dissemination was stopped in order to allow the concentration of *B. globigii* to reach homogeneity in the chamber. A Climet CI-500 aerosol particle sizer (Climet Instrument Co., Redlands, Calif.) was used to track the particle size distribution throughout the test (See FIG. 1). After the 60 minute sampling, the chamber air was purged clean, and the agar plants were removed and incubated for 15 hours at 35° C. Colonies were counted after the incubation period, and the baseline curve for *B. globigii* was established (See FIG. 2).

3. *B. globigii* Dissemination Followed by a Low Concentration Powder Dispersion

Figure 3:
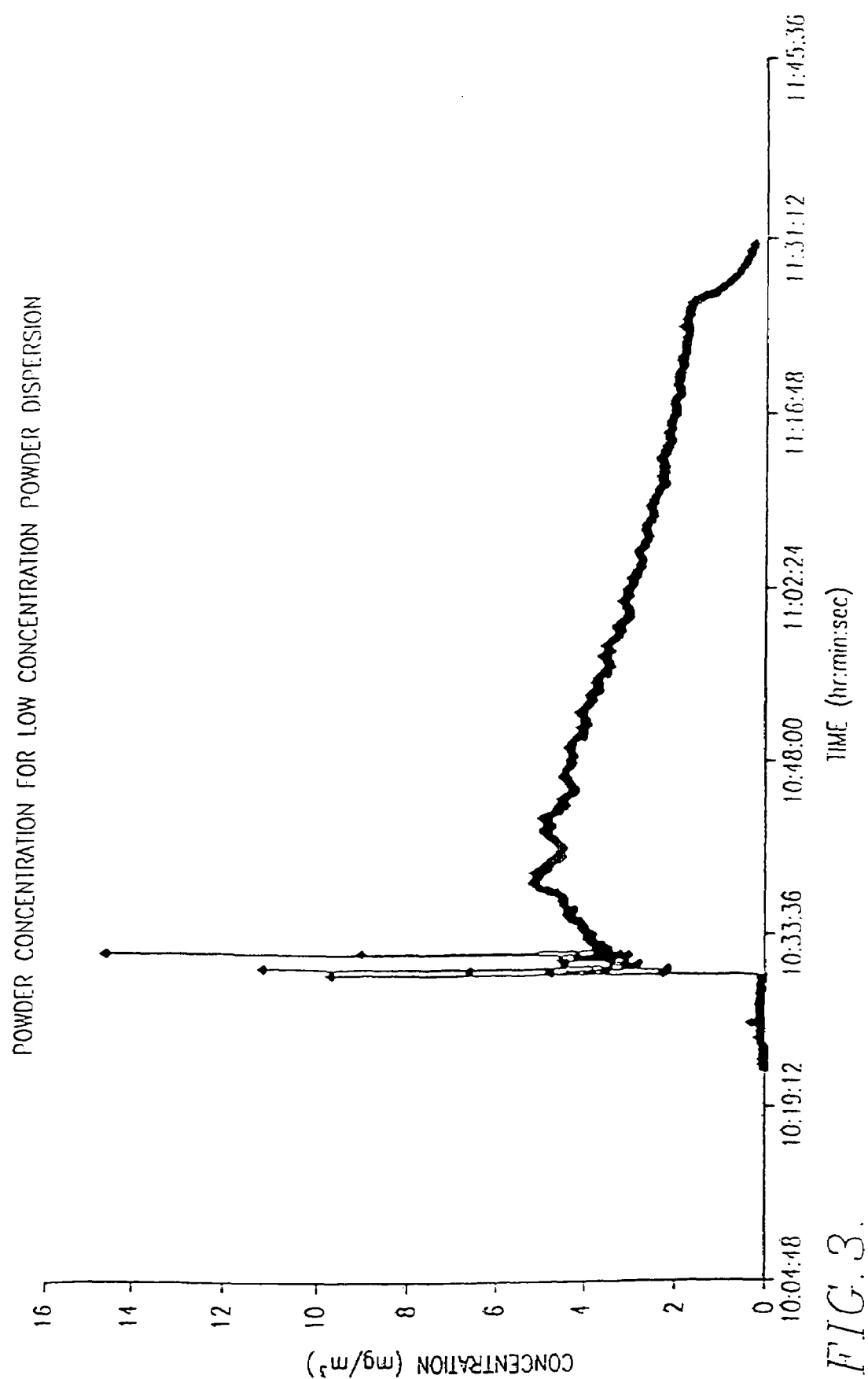
FIG. 3 is a graph depicting the Cl/AP-MgO concentration with respect to time when B. globigii was exposed to a low concentration of Cl/AP-MgO.

*B. globigii* was disseminated following the procedures described in Part 2 of this example. One minute after dissemination, sampling was commenced using the New Brunswick air samplers. Sampling was continued for 60 minutes. Five minutes after sampling was commenced, dispersion of Cl/AP-MgO powder (prepared as described in Example 2, Part 1) was initiated using a GEM-T air mill powder disperser (Coltec Industrial Products, Inc., Newtown, Pa.) and a vibrating spatula (Mettler Toledo, Highstown, N.J.). The powder was dispersed at a pressure of 40 psi until the concentration of powder in the air chamber reached approximately 4-5 mg/m$^3$ as indicated by a TSI Dustrak aerosol mass monitor (TSI, Inc., St. Paul, Minn.). These results are shown in FIG. 3. The particle size distributions were tracked using the Climet CI-500 (See FIG. 4). At this powder concentration, the air mill was stopped.

At the end of the 60 minute sampling period, the chamber air was purged clean, and the Casitone agar plates were removed and incubated for 15 hours at 35° C. Colonies were counted after the incubations period and a decay curve for *B. globigii* was determined (See FIG. 5).

Figure 6:
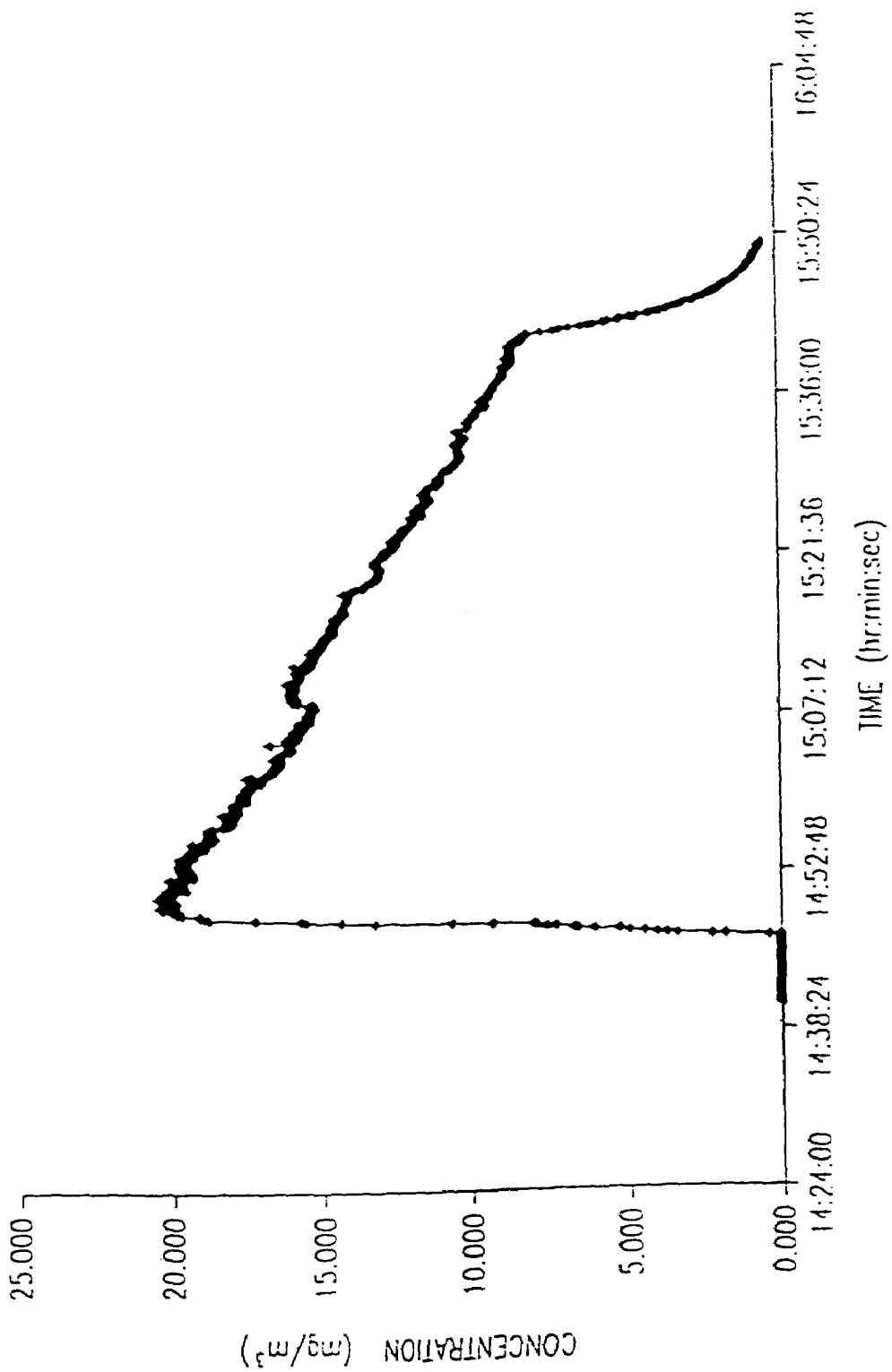
FIG. 6 is a graph depicting the Cl/AP-MgO concentration with respect to time when B. globigii was exposed to a high concentration of Cl/AP-MgO.

4. *B. globigii* Dissemination Followed by a High Concentration Powder Dispersion The procedure described in Part 3 of this example was repeated with the exception that the powder was dispersed to a concentration of approximately 20 mg/M$^3$, as shown in FIG. 6. FIG. 7 sets forth the particle size distribution and FIG. 8 sets forth the decay curve for *B. globigii* with a high concentration of Cl/AP-MgO powder dispersion.

5. Results and Discussion

Figure 2:
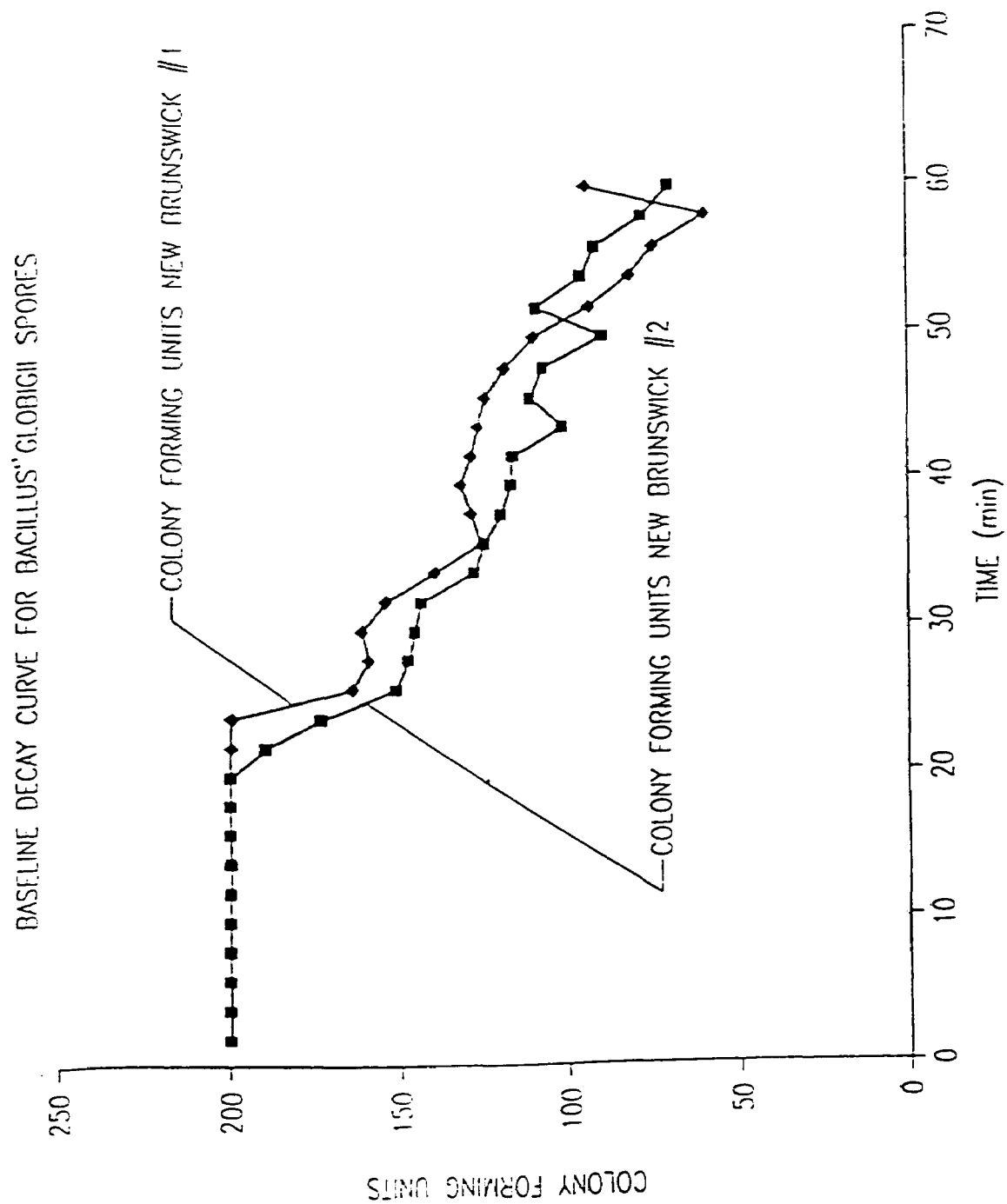
FIG. 2 shows the baseline decay curve for B. globigii.
Figure 5:
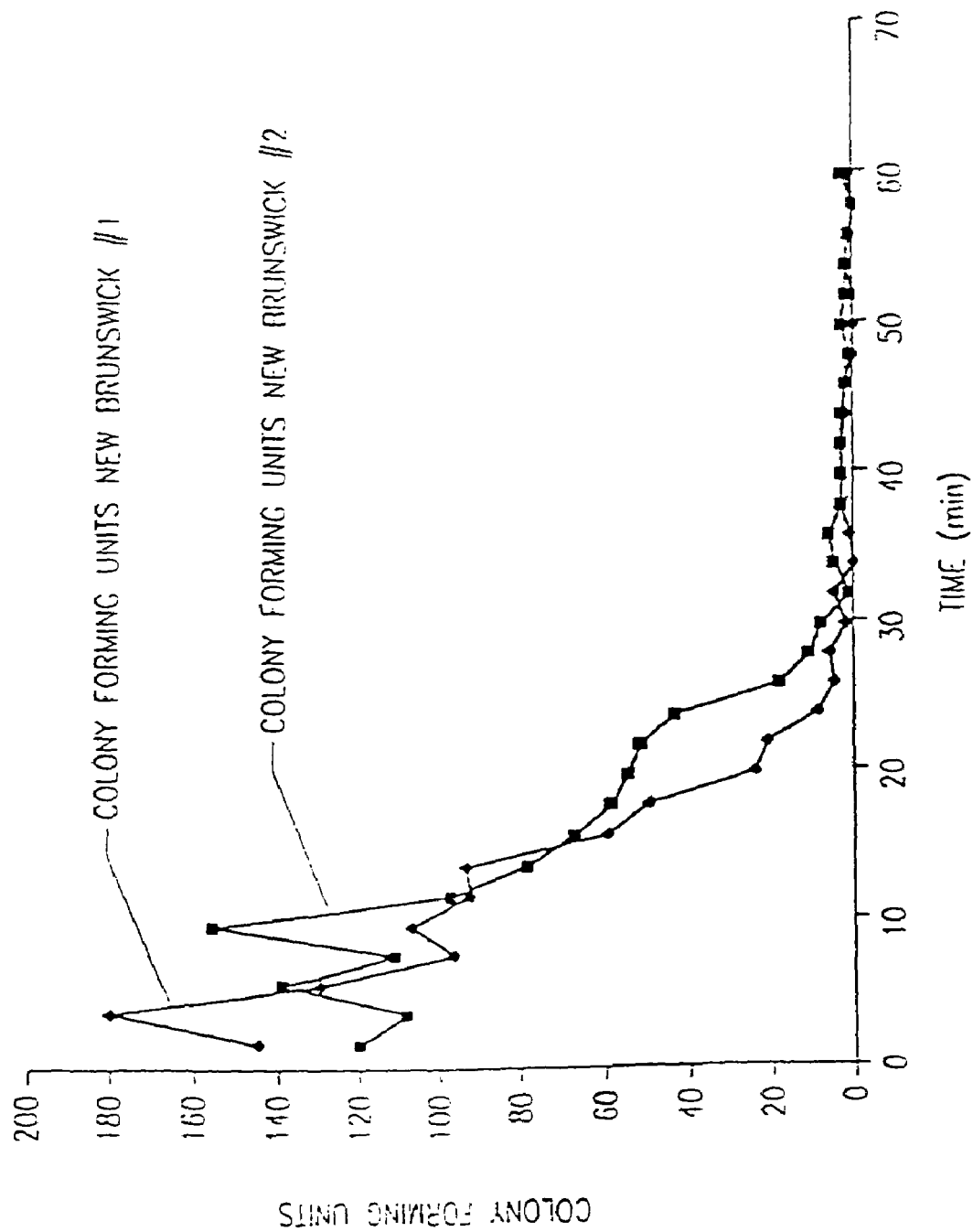
FIG. 5 shows the decay curve for B. globigii when B. globigii was exposed to a low concentration of Cl/AP-MgO.
Figure 8:
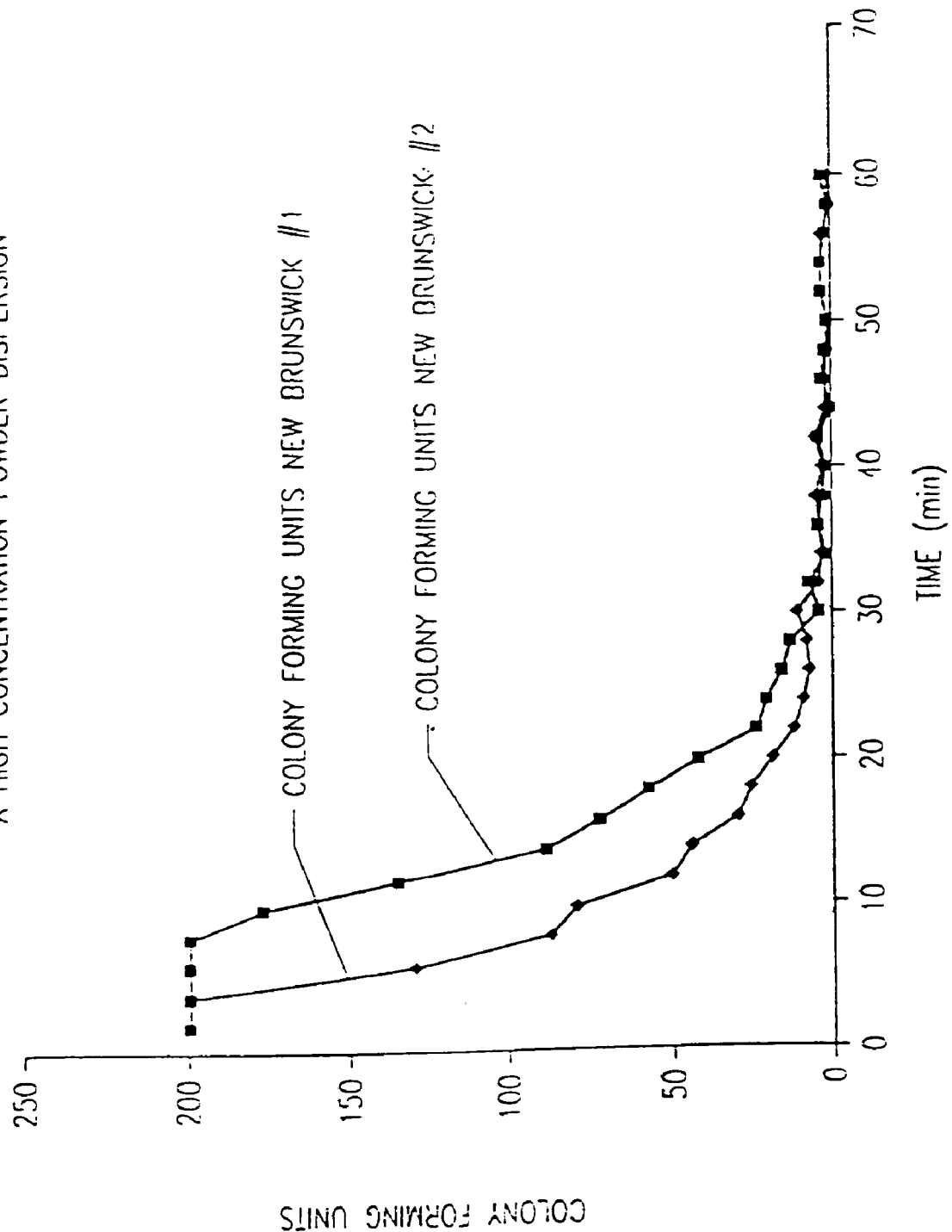
FIG. 8 is a graph illustrating the decay curve for B. globigii when B. globigii was exposed to a high concentration of Cl/AP-MgO.

The results of the tests conducted in Parts 2-4 of this example are shown in FIGS. 1-8. In FIGS. 2, 5, and 8, the y-axis indicates the number of *B. globigii* colony forming units (CFU's) collected in 100 liters of air at the given time point indicated on the x-axis. CFU measurements of 200 indicate that there were too many CFRs to count, and thus the maximum number of 200 was assigned. In FIG. 2, the baseline decay curve indicates that the concentration of viable cells in the chamber remained relatively high, starting at above 200 CFU per 100 liters of air sampled and decreasing to approximately 65 CFU per 100 liters of air sample during an one hour period. In the presence of a low concentration of Cl/AP-MgO powder, the decay curve of *B. globigii* indicates that the CFUs started high at about 180 CFU per 100 liters of air sampled and decreased to less than 20 CFU per 100 liters of air sampled in about 23 minutes (FIG. 5). Finally, the decay curve of *B. globigii* in the presence of a high concentration of Cl/AP-MgO powder indicates that the CFUs started off very high at above 200 CFU per 100 liters of air sampled and decreased sharply to less than 20 CFU per 100 liters of air sample in about 20 minutes (FIG. 8). A comparison of the decay curves of *B. globigii* (FIGS. 2, 5, and 8) indicates that the presence of metal oxide nanocrystals having reactive atoms stabilized on their surfaces has a significant impact on the number of viable cells recovered from the chamber environment. The data from Parts 3 and 4 above show that, as the concentrations of powder are increased, a more rapid decrease in the recovery of viable cells is obtained.

EXAMPLE 4A

*Bacillus cereus* bacterial endospores were grown and placed in water to form a suspension. A sterile nitrocellulose filter paper (3 cm diameter) was placed on a sterile rack, and 200 μl of the aqueous spore suspension was distributed onto the filter paper. The filter was air dried for 2-4 hours. The dried filter paper was placed in a sterile beaker, and 10 ml of LB (Luria and Bertani) broth (containing 10 g/L tryptone, 5 g/L yeast extract, and 10 g/L sodium chloride, pH adjusted to 7 with 5 N NaOH, and sterilized by pressurizing to about 1500 psi) were placed in another sterile beaker. The latter beaker was covered with aluminum foil. One gram of CP-CaO, was spread on the filter paper so that all of the paper was covered, aluminum foil was placed on top of this beaker, and the beaker was allowed to stand for 2 hours. Using tweezers, the filter paper was removed and excess nanoparticle powder gently shaken off. The filter paper was immersed in the LB broth solution for 10 minutes with occasional swirling. Ten μl of the LB broth solution was extracted by a sterile syringe and distributed evenly on a Benzer agar culture plate using a sterile L-shaped glass piece. The lid was placed on the agar plate, and the sample was incubated for 12 hours at 37° C. Three agar plates were prepared for each test. After incubation, the number of visible, living bacterial colonies was counted, and the percent killed or biocidally adsorbed (reduced) was determined using the following equations:

$$\text{Average Number of Colonies}=n_{avg}=(n_1+n_2+n_3)/3\% \text{ of Microorganisms Reduced}=n_{\%}=(n_C-n_E)/n_C\times 100,$$

where $n_E$=average number of colonies on experimental plates, and where $n_C$=average number of colonies on control plates.

The above procedures were repeated using Cl/AP-MgO, I/AP-MgO, AP-CaO with vacuum dehydration, and AP-CaO with $N_2$ dehydration in place of CP-CaO. The results are set forth in Tables 1 and 2 below:

TABLE 1

Results of two hour[a] exposure - raw data.[b]

| Reagent | Number of colonies on each plate | | | Average | % Reduced |
|---|---|---|---|---|---|
| Control | 78(72) | 40(99) | 87 | 68(80) | 0% |
| AP—CaO(vac) | 37 | 24 | 32 | 31 | 64 |
| AP—CaO($N_2$) | 18 | 29 | 34 | 27 | 68 |
| CP—CaO | 49(72) | 31(73) | 45(81) | 42(75) | 39(12) |
| AP—MgO—$Cl_2$ | 4(0) | 3(8) | 5(22) | 4(10) | 94(88) |
| AP—MgO—$I_2$ | 32(85) | 48(83) | 44(100) | 41(91) | 40(−7)[c] |

[a]Refers to the time period beginning when the particular metal oxide powder was placed on the filter containing bacteria and ending when the filter was placed in the LB broth.
[b]Numbers in parentheses are for repeated experiments with new reagents on a different day.
[c]A negative number indicates enhanced growth.

TABLE 2

Results of two hour[a] exposure - raw data.

| Reagent | Number of colonies on each plate | | | Average | % Reduced |
|---|---|---|---|---|---|
| Control | 500 | 652 | 736 | 633 | 0% |
| AP—MgO—$Br_2$ | 60 | 50 | 46 | 52 | 95 |

[a]Refers to the time period beginning when the Br/AP—MgO powder was placed on the filter containing bacteria and ending when the filter was placed in the LB broth.

EXAMPLE 4B

This experiment was conducted to determine the effect of exposing *B. cereus* to nanocrystalline metal oxides for varying lengths of time. The procedure described in Example 4 was repeated using Cl/AP-MgO powder and contacting the Cl/AP-MgO powder with the *B. cereus* for 0 (control), 20, 40, 60, 80, and 100 minutes. The results of this set of tests are set forth in Table 3.

TABLE 3

Results of variable time exposure for Cl/AP—MgO adduct.

| Time of Exposure[a] (min) | Number of colonies on each plate | | | Average | % Reduced |
|---|---|---|---|---|---|
| 0(control) | 100 | 107 | 120 | 109 | 0% |
| 20 | 5 | 4 | 8 | 6 | 95 |
| 40 | 6 | 3 | 14 | 8 | 93 |
| 60 | 3 | 4 | 1 | 3 | 98 |
| 80 | 5 | 6 | 4 | 5 | 95 |
| 100 | 8 | 5 | 3 | 5 | 95 |

[a]Refers to the time period beginning when the Cl/AP—MgO powder was placed on the filter containing bacteria and ending when the filter was placed in the LB broth.

Discussion

The results of the tests conducted in Examples 4A and 4B confirm that Cl/AP-MgO is a very effective reagent for the biocidal destruction of *B. cereus* spores and supports the data reported in the previous examples above on the biocidal destruction of *B. globigii*. Furthermore, Cl/AP-MgO acts rapidly, and even a 20 minute exposure was enough for efficient decontamination. Br/AP-MgO and AP-CaO were also quite effective in their biocidal abilities.

EXAMPLE 5

Figure 9:
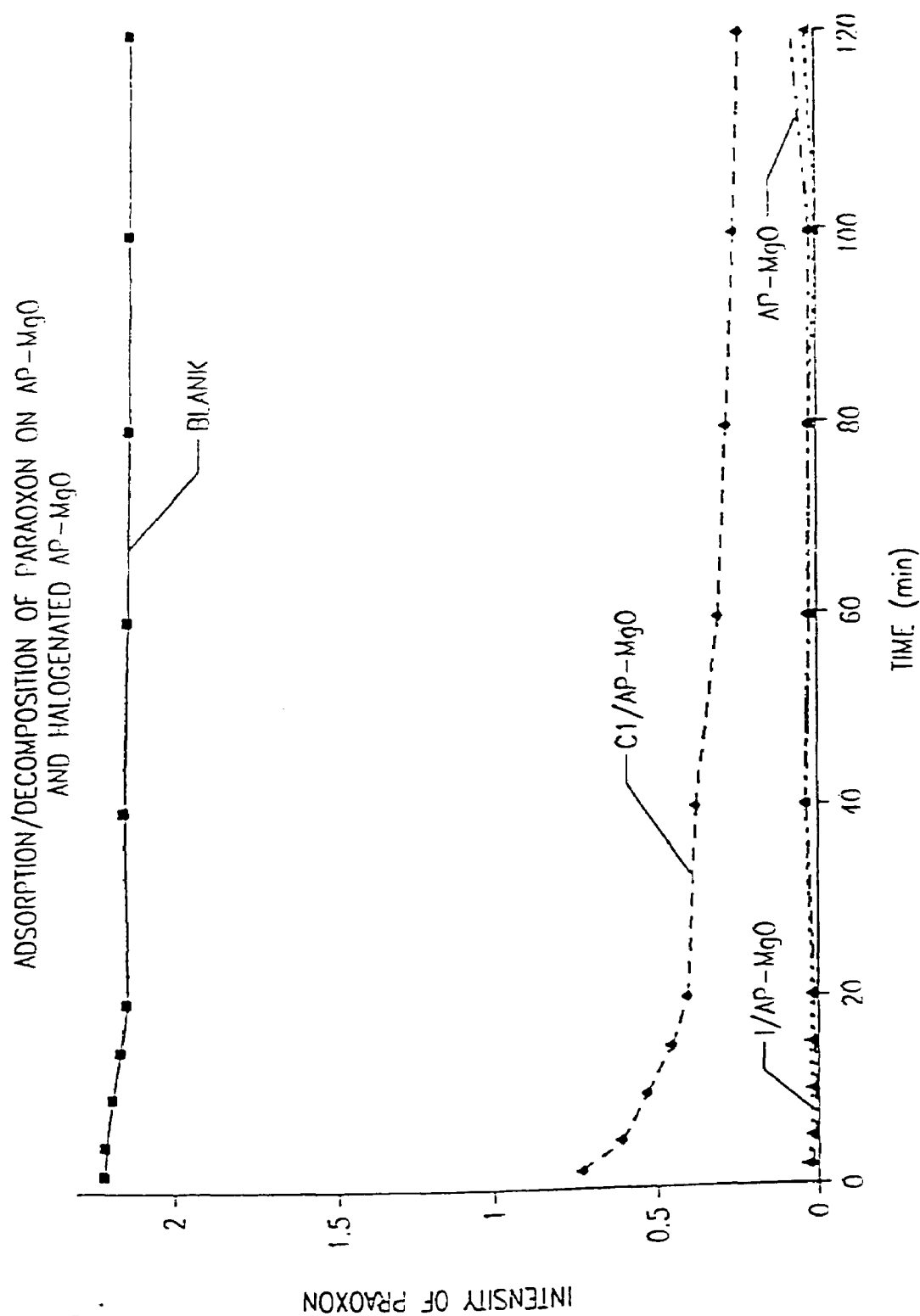
FIG. 9 is a graph illustrating the destructive adsorption of paraoxon on AP-MgO, I/AP-MgO, and Cl/AP-MgO.

0.1 g of AP-MgO, I/AP-MgO, or Cl/AP-MgO was placed in a flask equipped with a magnetic stirrer with 100 ml of pentane. A VX chemical agent mimic, paraoxon (4.5 µl), was added to the flask, with 2 ml of the resulting sample being withdrawn and the UV spectrum taken at 2, 5, 10, 15, 20, 40, 60, 80, 100, and 120 minutes after addition of the paraoxon. These results are illustrated in FIG. 9 and indicate that all three of the metal oxide samples worked well at destructively adsorbing the paraoxon. Upon reaction with paraoxon, the color of the sample (AP-MgO) changed from slightly grayish to bright yellow.

After the destructive adsorption of paraoxon was carried out, quantities of the AP-MgO/paraoxon samples were placed in solvents (methylene chloride or toluene) and sonicated for 30 minutes. After sonication, some of the liquid was removed from each sample and tested by GC-MS. The GC-MS results did not show the presence of paraoxon, thus providing evidence that the paraoxon was destructively adsorbed by the metal oxide samples. Similar results have been achieved when using non-modified nanocrystalline metal oxide particles to destructively adsorb 2-chloroethyl ethyl sulfide (2-CEES), diethyl4-nitrophenylphosphate (paraoxon), and dimethylmethylphosphonate (DMMP) as reported in U.S. patent application Ser. No. 08/914,632 (continuation-in-part of U.S. patent application Ser. No. 08/700,221), incorporated by reference herein.

EXAMPLE 6

In order to prepare metal oxide particles (e.g., AP-MgO, AP-CaO, etc.) having species adsorbed on the surfaces of the particles, 10 grams of the desired metal oxide is placed on a Schlenk flask. The air is evacuated, and the gaseous species is introduced. The sample is allowed to react for about 30 minutes, after which time the excess gaseous species is pumped out. Gaseous species which can be adsorbed on the surfaces of metal oxide particles include oxides of Group V and VI elements (such as $NO_2$ and $SO_2$, respectively) and ozone.

EXAMPLE 7

1. Materials

Aflatoxins are toxic and carcinogenic substances produced by certain strains of the molds *Aspergillus flavus* and *Aspergillus parasiticus*. For these examples, Aflatoxins were obtained from Sigma Chemical Company (St. Louis, Mo.). A 1,000 ppm stock solution of AB1 was prepared in acetonitrile. Serial dilutions of the stock solutions were made to obtain 100 ppm, 10 ppm, 1 ppm, 100 ppb, and 10 ppb working standard solutions. The nanoparticles evaluated for their detoxification capabilities were CP-MgO—$Br_2$ (100% saturation, i.e., 15% by weight bromine, AP-CaO—$Cl_2$ (100% saturation, 13% by weight chlorine), and AP-MgO—$Cl_2$ (100% saturation, 13% by weight chlorine). Appropriate control nanoparticles (non-halogenated nanoparticles and commercial MgO or CaO), positive control (AB1 without exposure to nanoparticles) and negative control (nanoparticle treatment only) were also evaluated in these studies.

2. Experimental Procedure

Fifty microliters of 10 ppm, 1 ppm, 100 ppb, and 10 ppb AB1 solutions were spiked onto a filter paper and placed in a glass jar. The filter paper was then exposed to the appropriate nanoparticles for 1 minute, and the glass jar was shaken to ensure uniform exposure to the nanoparticles. The filter paper was removed from the jar, shaken to dust off the nanoparticles, and placed in an Agri-Screen (obtained from Neogen, Lansing, Mich.) solvent extraction bottle for 1 minute with frequent mixing of the bottle content. Approximately 2 ml of the extraction solvent was then passed through a syringe equipped with glass wool and collected in a sample collection bottle.

Following the Aflatoxin AB1 extraction, an Agri-Screen kit (which included a conjugate solution, a stop solution, and a substrate) was used to screen for residual Aflatoxin in the extraction solvent. An Agri-Screen kit is a competitive, direct enzyme-linked immunosorbent assay (CD-ELISA) that allows the qualitative, visible testing of a sample against a known control concentration. Free toxin, both in the sample and in the control, is allowed to compete with the enzyme-labeled toxin (conjugate) for the antibody binding sites. After a wash step, the substrate is added, and it reacts with the bound enzyme conjugate to produce a blue color. The color of the sample is then visually compared to the color of the control. If the sample color is more blue than the control, then it contains less toxin than the control. If the sample color is less blue than the control, then it contains more toxin than the control.

Thus, the Agri-Screen procedure in this example consisted of adding 3 drops of the sample solvent to the well followed by the addition of 2 drops of a conjugate solution. The wells were then incubated for 5 minutes at room temperature. Three drops of substrate were added to the wells and incubated for 5 minutes at room temperature followed by the addition of a stop solution. The contents of the well were mixed with the Pasteur pipette, and the color of the solution in the well was recorded. The color of the solution in the well was compared to that of the solution in the control wells (20 ppb Aflatoxin B1).

3. Results

The results of these tests are summarized in Table 4. The halogenated metal oxide nanoparticles inhibited the growth of toxins. These results, when viewed with the results of the previous examples, indicate that the halogenated metal oxide nanoparticles are effective as decontaminating agents active against a broad class of both chemical and biological species.

The exact mechanism by which decontamination occurs is not known. However, it is believed that the nanoparticles are attacking either the ketone or methoxy group of the Aflatoxin (see Formula I).

TABLE 4

Effect of Nanoparticles on Aflatoxin B1.

| Nanoparticle | Result | Nanoparticle | Result |
|---|---|---|---|
| Kit control | + | | |
| Nanoparticle only (control) | -- | | |
| Aflatoxin B1 (AB1) 10 ppm | + | | |
| CM-MgO (10 ppm AB1) | -- | AP-MgO-$Cl_2$ (10 ppm AB1) | -- |
| CM-MgO (1 ppm AB1) | -- | AP-MgO-$Cl_2$ (1 ppm AB1) | -- |
| CM-MgO (100 ppb AB1) | -- | AP-MgO-$Cl_2$ (100 ppb AB1) | -- |

TABLE 4-continued Effect of Nanoparticles on Aflatoxin B1.

| Nanoparticle | Result | Nanoparticle | Result |
|---|---|---|---|
| CP-MgO (100 ppb AB1) | – | CM-CaO (100 ppb AB1) | –– |
| CP-MgO (10 ppb AB1) | – | CM-CaO (10 ppb AB1) | –– |
| CP-MgO-$Br_2$ (10 ppm AB1) | –– | AP-CaO (10 ppm AB1) | –– |
| CP-MgO-$Br_2$ (1 ppm AB1) | –– | AP-CaO (1 ppm AB1) | –– |
| CP-MgO-$Br_2$ (100 ppb AB1) | –– | AP-CaO (100 ppb AB1) | –– |
| CP-MgO-$Br_2$ (10 ppb AB1) | –– | AP-CaO (10 ppb AB1) | –– |
| AP-MgO (10 ppm AB1) | –– | AP-CaO-$Cl_2$ (10 ppm AB1) | –– |
| AP-MgO (1 ppb AB1) | –– | AP-CaO-$Cl_2$ (1 ppm AB1) | –– |
| AP-MgO (100 ppb AB1) | –– | AP-CaO-$Cl_2$ (100 ppb AB1) | –– |
| AP-MgO (10 ppb AB1) | –– | AP-CaO-$Cl_2$ (10 ppb AB1) | –– |

+ Sample had more Aflatoxin B1 than the control well (20 ppb AB1)
– Sample had about the same concentration of Aflatoxin B1 as the control well (20 ppb AB1)
–– Sample had less Aflatoxin B1 than the control well (20 ppb AB1)

Formula IV

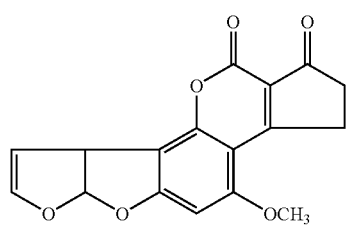

EXAMPLE 8

1. Procedure

In this test, metal oxide powders (in the amounts shown in Table 5) were added to 1 liter of distilled water contaminated with *E. coli* (ATCC#3000, approximately 400 μl of a fresh, overnight culture). Controls (200 μl) were plated on nutrient agar before (time equal zero) and during the test to determine a baseline. At the given time interval, 200 μl of the decontaminated water was sampled and plated on nutrient agar and incubated for 24 hours. Plates were counted and compared to the controls to determine the percent kill.

2. Results

The metal oxide nanoparticles were successful in decontaminating gram-negative. bacteria such as *E. coli*. Table 5 compares the three different formulations of metal oxide or hydroxide nanoparticles. High surface area AP-MgO (greater than about 300 $m^2/g$) and ZnO (greater than about 130 $m^2/g$) samples were very effective at destructively sorbing the *E. coli*.

TABLE 5

| | Metal Oxide | | | | | |
|---|---|---|---|---|---|---|
| | AP—$Ca(OH)_2$ | ZnO | ZnO | ZnO | AP—MgO | AP—MgO |
| | Surface area | | | | | |
| | 60 $m^2/g$ | 153 $m^2/g$ | 153 $m^2/g$ | 153 $m^2/g$ | 642 $m^2/g$ | 452 $m^2/g$ |
| | Amount | | | | | |
| | 0.75 g | 1 g | 1 g | 0.5 g | 1 g | 1 g |
| Time (minutes) | Percent Kill | Percent Kill | Percent Kill | Percent Kill | Percent Kill | Percent Kill |
| 15 | 98 | 99.6 | 100 | 61 | 54 | 60 |
| 30 | 100 | 99 | 100 | 63 | 100 | 100 |
| 45 | 100 | 99.8 | 100 | 73 | 100 | 100 |
| 60 | 100 | 96.7 | 100 | 48 | 100 | 100 |

EXAMPLE 9

1. Preparation of ZnO-Coated AP-MgO (hereinafter referred to as AP-MgO/ZnO)

In this procedure, 2.28 g of zinc acetate was dissolved in approximately 200 ml of ethanol and 6 ml of distilled water. This solution was then added to 14.5 g of AP-$Mg(OH)_2$. After nitrogen was introduced into the mixture for 20 minutes, the flask was capped and left to stir overnight. The sample was then filtered, washed with ethanol, and filtered again. The filtered product, ZnO-coated AP-$Mg(OH)_2$, was then activated using a dehydrator to produce ZnO-coated AP-MgO nanoparticle powder. Approximately 10 g of ZnO-coated AP-MgO of 5 mole percent by mass ZnO was obtained. The resulting BET surface area was 446 $m^2/g$.

2. Preparation of CuO

Under argon, 1.50 g (0.0112 mole) of copper (II) chloride (obtained from Sigma Aldrich) was added to a 250 ml round bottom flask. This was then dissolved with 70 ml absolute ethanol (obtained from McCormick) to form a clear green solution. Next, 0.0224 mole sodium hydroxide (obtained from Fisher) was dissolved in absolute ethanol and was then added dropwise to the clear green solution to form the copper hydroxide gel. The reaction was stirred at room temperature for 2 hours. During this time, the reaction mixture formed a blue-green gel. After the reaction was complete, the solution was filtered and washed with water to remove the sodium chloride. The copper hydroxide was then air-dried on the frit, to give a 90% yield. Data from thermal gravimetric analysis (TGA) confirmed that the copper hydroxide to copper oxide conversion occurred between 190-220° C. The dry copper hydroxide powder was then placed into a Schlenk tube, connected to a flow of argon and surrounded by a furnace. The furnace was connected to a temperature controller, and it was heated at 250° C. for 15 minutes. After the heat treatment was complete, the furnace was turned off and allowed to cool to room temperature. The copper oxide powder was black with a BET specific surface area of 135 $m^2/g$.

3. Preparation of $[Ce(NO_3)_3-Cu(NO_3)_2]TiO_2$

In this procedure, 211 ml of neat titanium (IV) butoxide was added to 800 ml of methanol and flushed with nitrogen while stirring for 10 minutes in a round bottom flask. A second, water-containing solution, was then prepared with 300 ml of methanol, 45 ml of distilled water, and 2.2 ml of nitric acid. This solution was added dropwise to the stirring butoxide solution. A gel slowly formed and was allowed to age overnight. Once the gel had aged, methanol was added at a 1:1 ratio and mixed, thus forming a solution that was spray dried (Buchi 190) with an inlet temperature of 200° C. and an outlet temperature of 80° C. The spray-dried powder was collected and washed in 800 ml of distilled water overnight and centrifuged to remove any excess solvent. The $TiO_2$ was dried in an oven to remove any excess water. Approximately 20 g of $TiO_2$ was obtained, and the resulting BET surface area was 194.2 $m^2/g$.

Ten grams of $TiO_2$ was then coated with $Ce(NO_3)_3$ and $Cu(NO_3)_2$. To accomplish this, 0.544 g of $Ce(NO_3)_3$ and 0.291 g of $Cu(NO_3)_2$ were weighed out in a dry flask, and 100 ml of TF was then added to dissolve the nitrates. Next, 10 g of $TiO_2$ was added, and the solution was stirred for 2 hours. The $TiO_2$ was allowed to settle for approximately one hour after which the THF was decanted off the solution. The flask was then stopped and put on a vacuum line overnight to remove the remainder of the THF. After the sample vacuum step was completed, the sample was placed uncapped in a drying oven set at 110° C. for 1 hour. The resulting BET surface area of the 1 mole % $Ce(NO_3)_3$/1 mole % $Cu(NO_3)_2$ $TiO_2$ nanoparticle formulation was 191 $m^2/g$.

4. Procedure

Nanoparticle metal oxides prepared in Parts 1-3 of this Example were tested for their abilities to destructively sorb or decontaminate biological warfare mimics. In each trial run, nitrocellulose membranes were inoculated with 200 µl B. subtilus spores solution or a gram negative bacteria (E. coli or E. herbicola) suspension and allowed to dry for approximately 1 hour. After 1 hour, each membrane was inoculated with 0.5 g of nanoparticles. Samples were taken at different time intervals. After the desired contact time was reached, the membranes were rinsed in 10 ml of PBS to elute the spores. Next, 200 µl of the final solution was plated onto nutrient agar plates and incubated for 24 hours at 37° C. Colonies were counted and compared to the controls to determine the percent kill.

5. Results

Tables 6-8 set forth these results. Table 6 illustrates that the metal oxides were able to inactivate bacterial spores, while Tables 7 and 8 indicate that metal oxides readily decontaminate or destroy gram-negative bacteria, even in less than an hour or a matter of minutes.

TABLE 6

Decontamination of B. subtilis Spores Using Nanoparticle Powders

| | Metal Oxide | | |
|---|---|---|---|
| | ZnO | CuO | $[Ce(NO_3)_3-Cu(NO_3)_2]TiO_2$ |
| | Surface area | | |
| | 153 $m^2/g$ | 135 $m^2/g$ | 191 $m^2/g$ |
| | Amount | | |
| Time (minutes) | 0.5 g Percent Kill | 0.5 g Percent Kill | 0.5 g Percent Kill |
| 10 | 84.6 | -- | 95 |
| 20 | 88.2 | -- | 97 |
| 30 | 97.2 | -- | 83 |
| 45 | -- | -- | 84 |
| 60 | -- | 99.6 | 81 |

TABLE 7

Decontamination of E. coli and Erwinia herbicola After Exposure to Nanoparticles for 24 Hours

| | Metal Oxide | | | |
|---|---|---|---|---|
| | AP-MgO | AP-CaO | AP-MgO/ZnO[a] | CP-MgO/ZnO[b] |
| | Amount | | | |
| Bacteria | 0.5 g Percent Kill | 0.5 g Percent Kill | 0.5 g Percent Kill | 0.5 g Percent Kill |
| E. coli | 100 | 100 | 100 | 100 |
| E. herbicola | 40 | 100 | 100 | 100 |

[a]A coating of ZnO on MgO.
[b]A coating comprisng a mixture of MgO and ZnO.

TABLE 8

Decontamination of Erwinia herbicola After Exposure to Nanoparticles for 1 Hour

| | Metal Oxide | | | |
|---|---|---|---|---|
| | AP-MgO | AP-MgO | CP-MgO | AP-MgO/ZnO |
| | Amount | | | |
| Bacteria | 0.5 g Percent Kill | 0.5 g Percent Kill | 0.5 g Percent Kill | 0.5 g Percent Kill |
| E. herbicola | 100 | 93 | 100 | 79 |

EXAMPLE 10

1. Procedure

In this example, metal oxide nanoparticles (in a propellant) were tested for their abilities to decontaminate various textured surfaces. The concentration of B. subtilis spores was first determined by plating serial dilutions of the stock solution and counting the number of colonies that appeared on the corresponding plates. A concentration of $1.40 \times 10^8$ CFU/ml was obtained. The solution was then placed in a spray bottle to disperse the spores onto the various surfaces. The multiple panes were placed into the biochamber for safety precautions. Each panel was contaminated with a concentration of spores that was about $1.4 \times 10^8$ CFU/ml. The spores were allowed to dry on the panels for 24 hours before decontamination took place. After the drying period, the panels were sprayed with a solution containing metal oxide nanoparticles (2 grams of powder in 200 ml of either pentane or water) via a hand-held tank compressed with nitrogen gas.

After the 24-hour decontamination period, the panels were tested using a PBS moistened swab. The swab was then placed into 20 ml of PBS, and the solution was allowed to elute for 30 minutes. The solution was serially diluted $10^{-1}$, $10^{-2}$, $10^{-3}$, $10^{-4}$, $10^{-5}$, and $10^{-6}$, respectively, in 9 ml of PBS and 200 μl of each dilution was plated onto nutrient agar in triplicate to evaluate growth. After the 24-hour incubation period, the colonies were counted, and the percent kill was calculated for each textured panel.

2. Results

Table 9 sets forth these results. AP-MgO was successful with every surface except the office panel. Overall, ZnO in water did not decontaminate as well as the AP-MgO, but it was able to successfully decontaminate the office panel and was also better at decontaminating the metal panel. These results should be even better with a solution containing higher concentrations of the nanoparticles.

TABLE 9

| Textured Surface | AP-MgO in Pentane | ZnO in Water |
|---|---|---|
| Wallboard | 98 | 63 |
| Metal Panel | 85 | 92 |
| Ceiling Tile | 91 | 84 |
| Office Panel | 0 | 92 |
| Cement | 99 | 64 |
| Carpet | 99 | 81 |

EXAMPLE 11

1. Procedure

A suspension of tryptone yeast extract (TYE) broth was prepared with a single colony from a *E. coli* (C3000, ATCC#15597) plate and incubating it for 18 hours at 37° C. The lysate was treated with AP-MgO by adding 0.009 g of powder/700 μl of diluted MS2 virus (a simulant of human enteric viruses). Approximately 300-500 μl of the *E. coli* and 100 μl of the treated lysate were added to a tube containing 2.5 ml TYE soft agar. The solution was placed in a water bath (50° C.) for approximately 10 minutes and poured onto a TYE agar plate that was allowed to dry for approximately 10 minutes followed by incubation at 37° C. This procedure was performed in serial dilutions up to a dilution of $10^{-10}$. The dilutions of $10^{-8}$ to $10^{-10}$ were plated for counting. The plaques were then counted, and the degree of killing was determined by comparing the number of countable plaque-forming units on the controls to the ones containing AP-MgO nanoparticles.

2. Results

The AP-MgO significantly affected the growth of the MS2 virus. These results are set forth in Table 10. Between three different dilution experiments, the lowest and highest percent kills were 96.5% and 100%, respectively.

TABLE 10

| Experiment[a] | Control Plaques (average) | Dilution Factor | Decontaminated Plaques (average) | Decontaminated Dilution Factor | % Recovery | % Kill |
|---|---|---|---|---|---|---|
| Trial 1 | 76.3 | 8 | 2.67 | 8 | 3.50 | 96.5 |
| Trial 2 | 74 | 9 | 0 | 9 | 0 | 100.0 |
| Trial 3 | 109 | 10 | 1 | 10 | 0.917 | 99.08 |

[a]AP—MgO - 0.009 g/700 μl; each trial was done in triplicate.

We claim:

1. A method of at least partially decontaminating an area subjected to an undesirable chemical or biological agent, comprising the step of spraying adjacent said area a mixture adapted for placement within a container, said mixture comprising particles selected from the group consisting of metal oxide particles, metal hydroxide particles, and mixtures thereof, said particles having a surface area of at least about 70 m²/g, and a propellant.

2. The method of claim 1, said metal oxides being selected from the group consisting of MgO, CeO$_2$, AgO, SrO, BaO, CaO, ZnO, Al$_2$O$_3$, TiO$_2$, ZrO$_2$, FeO, V$_2$O$_3$, V$_2$O$_5$, Mn$_2$O$_3$, Fe$_2$O$_3$, NiO, CuO, and Ag$_2$O and mixtures thereof.

3. The method of claim 2, said metal oxide comprising MgO.

4. The method of claim 1, said mixture including a suspension agent for said particles.

5. The method of claim 4, said suspension agent selected from the group consisting of pentane and water.

6. The method of claim 1, said particles comprising metal oxide composites made up of a first metal oxide at least partially coated with a second, different metal oxide.

7. The method of claim 1, said particles being present as a self-sustaining body formed of a plurality of agglomerated particles.

8. The method of claim 1, said propellant being nitrogen gas.

9. The method of claim 1, said area comprising a surface.

10. The method of claim 9, said surface comprising a textured surface of a member selected from the group consisting of wallboard, metal panel, ceiling tile, office panel, cement, and carpet.

11. The method of claim 1, said undesirable chemical or biological agent being an airborne agent.

12. A method of at least partially decontaminating an area subjected to an undesirable chemical or biological agent, comprising the step of spraying adjacent said area a mixture adapted for placement within a container, said mixture consisting essentially of particles selected from the group consisting of metal oxide and metal hydroxide particles and mixtures thereof, a suspension agent for said particles, and a propellant.

13. The mixture method of claim 12, said metal oxide and metal hydroxide parties each respectively selected from the group consisting of alkali metal, alkaline earth metal, transition metal, and lanthanide oxides and hydroxides and mixtures thereof.

14. The mixture method of claim 13, said metal oxides being selected from the group consisting of MgO, $CeO_2$, AgO, SrO, BaO, CaO, ZnO, $Al_2O_3$, $TiO_2$, $ZrO_2$, FeO, $V_2O_3$, $V_2O_5$, $Mn_2O_3$, $Fe_2O_3$, NiO, CuO, $SiO_2$, and $Ag_2O$ and mixtures thereof.

15. The method of claim 14, said metal oxide being MgO.

16. The method of claim 12, said suspension agent selected from the group consisting of pentane and water.

17. A method of at least partially decontaminating an area subjected to an undesirable chemical or biological agent, comprising the step of spraying adjacent said area a non-aqueous mixture adapted for placement within a container, said mixture comprising particles selected from the group consisting of metal oxide and metal hydroxide particles and mixtures thereof, said particles having an average crystallite size of up to about 20 nm, and a propellant.

18. The method of claim 17, said metal oxide and metal hydroxide parties each respectively selected from the group consisting of alkali metal, alkaline earth metal, transition metal, and lanthanide oxides and hydroxides, and mixtures thereof.

19. The method of claim 18, said metal oxides being selected from the group consisting of MgO, $CeO_2$, AgO, SrO, BaO, CaO, ZnO, $Al_2O_3$, $TiO_2$, $ZrO_2$, FeO, $V_2O_3$, $V_2O_5$, $Mn_2O_3$, $Fe_2O_3$, NiO, CuO, $SiO_2$, and $Ag_2O$ and mixtures thereof.

20. The method of claim 19, said metal oxide being MgO.

21. The method of claim 17, said mixture including a suspension agent for said particles.

22. The method of claim 21, said suspension agent selected from the group consisting of pentane and water.

\* \* \* \* \*